United States Patent [19]

O'Connell

[11] Patent Number: 4,709,694
[45] Date of Patent: Dec. 1, 1987

[54] GLOVE-LIKE DYNAMIC SPLINT AND METHOD OF USING SAME

[76] Inventor: Bonnie O'Connell, 11 Dover Ln., Old Bethpage, N.Y. 11804

[21] Appl. No.: 890,908

[22] Filed: Jul. 28, 1986

[51] Int. Cl.⁴ .......................... A61F 5/10; A61F 5/04
[52] U.S. Cl. .................................... 128/87 A; 128/77; 2/167
[58] Field of Search ...................... 128/77, 87 R, 87 A, 128/89 R, 26, 85, 167; 2/161 R, 161 A, 162, 163, 164, 159, 16, 21

[56] References Cited

U.S. PATENT DOCUMENTS

| 3,031,680 | 5/1962 | Compiano | 2/161 A |
| 3,098,237 | 7/1963 | Slimovitz | 2/164 |
| 3,890,649 | 6/1975 | Diggins | 2/16 X |
| 4,164,043 | 8/1979 | Fujita | 2/161 A |
| 4,561,122 | 12/1985 | Stanley et al. | 2/19 X |

Primary Examiner—Robert A. Hafer
Assistant Examiner—Kathleen J. D'Arrigo
Attorney, Agent, or Firm—McGlew and Tuttle

[57] ABSTRACT

A dynamic splint for treating the hands of persons with spastic conditions comprises a glove-like covering made of stretch material which covers the palm and the back of the hand. The covering includes one or more sleeve portions for receiving the thumb at least. A padding is provided over the metacarpal-phalangeal joint. Where the covering includes the index finger and an adjacent finger, the collar around each finger is provided with an accumulation of material or for facilitating extension of the index finger. The invention includes a method of treating people, in particular children, using the glove-like dynamic splint.

4 Claims, 3 Drawing Figures

GLOVE-LIKE DYNAMIC SPLINT AND METHOD OF USING SAME

FIELD AND BACKGROUND OF THE INVENTION

The present invention relates in general to the field of physiotherapy, and in particular to a new and useful dynamic splint and treatment method for the hands of a person suffering from a spastic condition.

In people suffering from a spastic condition such as cerebral palsy, the thumbs of the hands are often adducted. Adduction of the thumb is a condition where the thumb is closed in over the palm of the hand and is hyperextended. In such individuals the index finger may also flex into a useless position.

The foregoing conditions are extremely debilitating in that they prevent the individual from using a finger tip pinch action to grasp small objects between the tips of the thumb and forefinger. Other pinching actions of the human hand such as holding objects between the thumb and the index finger, or the index and the long fingers are also prevented. The individual is also unable to bring his or her hands into a so-called "beer can" position where a larger object can be engaged between the thumb and index finger and along the surfaces of the thumb and index finger.

To enable persons with spastic conditions to use their hands more efficiently, devices known as dynamic splints have been used which function to achieve thumb abduction wherein the thumb is spread out away from the palm and slightly flexed into a more useful position. Some dynamic splints also include structures for extending the index finger.

Known dynamic splints utilize pads which are interconnected by springs for engaging various parts of the hand. One such structure is known as the Oppenheimer spring wire splint. Such splints are available for example, from Fred Sammons, Inc. of Brookfield, Ill. These known dynamic splints are uncomfortable and cumbersome to wear. This situation is particularly aggravated in the case of a child with a spastic condition. It is particularly hard for children to tolerate wearing known dynamic splints. When supplied by the physiotherapist they are quickly removed by the child.

There is thus a clear need for a dynamic splint which functions to abduct the thumb and extend the index finger while being comfortable to wear.

This will be described in geater detail herein. The present invention involves the use of a glove-like structure for use as an effective dynamic splint for the hand.

U.S. Pat. No. 4,561,122 to Stanley et al discloses a sport's glove having specialized padding arrangements which incorporate slow recovery foam to maximize the ability of the glove to absorb shock or trauma inflicted upon vunerable areas of the hand. A palmar thumb pad is used, although the placement of the pad is somewhat different. No mention however, is made of restricting the movement of the thumb relative to the index finger. The glove is also made primarily of non-elastic material U.S. Pat. No. 4,525,877 to Chong discloses a sports glove including reinforcing patches in spots subjected to abrasion from the handling of a racquet. Here again, pads are applied over some areas of the thumb. The position of the pads is not intended for any therepeutic affect on the hand, nor is the glove made predominantly of elastic material so as to be stretched over the hand.

Glove-like splints for immobilizing the hand are also known from U.S. Pat. No. 4,281,647 to Antypas and U.S. Pat. No. 4,173,218 to Cronin. U.S. Pat. No. 4,378,009 to Rowley et al shows an inflatable structue for an injured part of the body including the hand.

Splint or brace structures are disclosed in U.S. Pat. No. 3,533,405 to Collins and U.S. Pat. No. 3,595,225 to Beeman. Both use springs and engagement pads and loops for various parts of the hand.

SUMMARY OF THE INVENTION

The present invention is directed to a glove-like dynamic splint and method of using the splint for treating people, and in particular children, suffering from a spastic condition.

One paramount advantage of the present invention is that the glove is comfortable and convenient to wear and does not, in and of itself, hinder the use of the hand. At the same time it effectively treats the problems of thumb adduction and flexing of the index finger, as well as causing a general relaxation of spasticity in the hand.

Accordingly, an object of the present invention is to provide a dynamic splint for treating the hands of a person having a spastic condition causing thumb adduction and hyperextension, comprising a covering of stretch material for covering at least part of the palm and part of the back of the person's hand, said covering having at least one sleeve portion with an opening therethrough for the person's thumb, said sleeve portion at least partly covering the metacarpal and proximal phalanx of the thumb, said covering including at least one web portion for extending between the thumb and the index finger of the person's hand, and a pad connected to said covering in a position for engagement over the metacarpal-phalangeal joint of the person's hand at the base of the thumb.

A further object of the invention is to provide the covering of stretch material with a second sleeve portion with a hole therethrough for the index finger of the person's hand. An accumulation of material is placed around the edge of the hole (like a donut with a hole in it). It has been found that this collar of material facilitates extension of the index finger.

A further object of the invention is to use such a glove-like dynamic splint in the treatment of a person having a spastic condition, particularly in the treatment of children. The treatment comprises application of the dynamic splint.

A further object of the invention is to provide a dynamic splint which is simple in design, rugged in construction and which includes no metal parts which contribute to discomfort and awkwardness in wearing the splint.

The various features of novelty which characterize the invention are pointed out with particularity in the claims annexed to and forming a part of this disclosure. For a better understanding of the invention, its operating advantages and specific object attained by its uses, reference is made to the accompanying drawings and descriptive matter in which preferred embodiments of the invention are illustrated.

DESCRIPTION OF THE PREFERRED EMBODIMENTS

Figure 1:
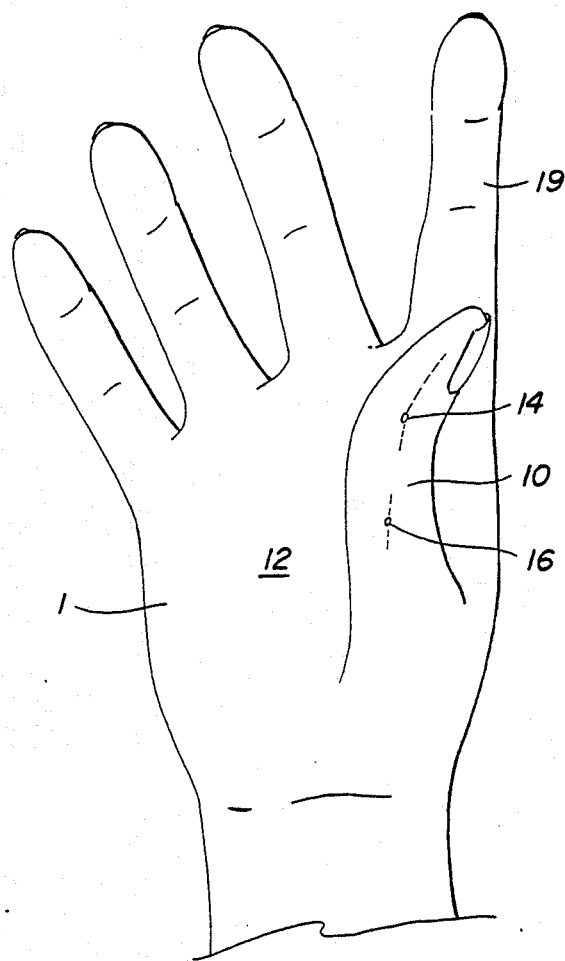
FIG. 1 is a palm side elevational view of the hand of a person, in particular a child, suffering from a spastic condition such as cerebral palsy.

Referring to the drawings in particular, FIG. 1 shows the hand of a child suffering from a spastic condition such as cerebral palsy where the thumb 10 of the hand 1 is adducted. In this position, the thumb is closed over the palm 12. The distal interphalengeal joint or DIP 14 of the thumb is also hyperextended.

In such a condition, the index finger 19 is often flexed. Together, these conditions prevent a pincer grasp or the ability to bring the tips of the thumb and index finger together to pick up an object.

FIG. 1 also shows the metacarpal-phalangeal joint 16 of the thumb 10. Joint 16 connects the metacarpal of the thumb to the proximal phalanx of the thumb. DIP joint 14 connects the proximal phalanx of the thumb to the distal phalanx of the thumb.

Figure 2:
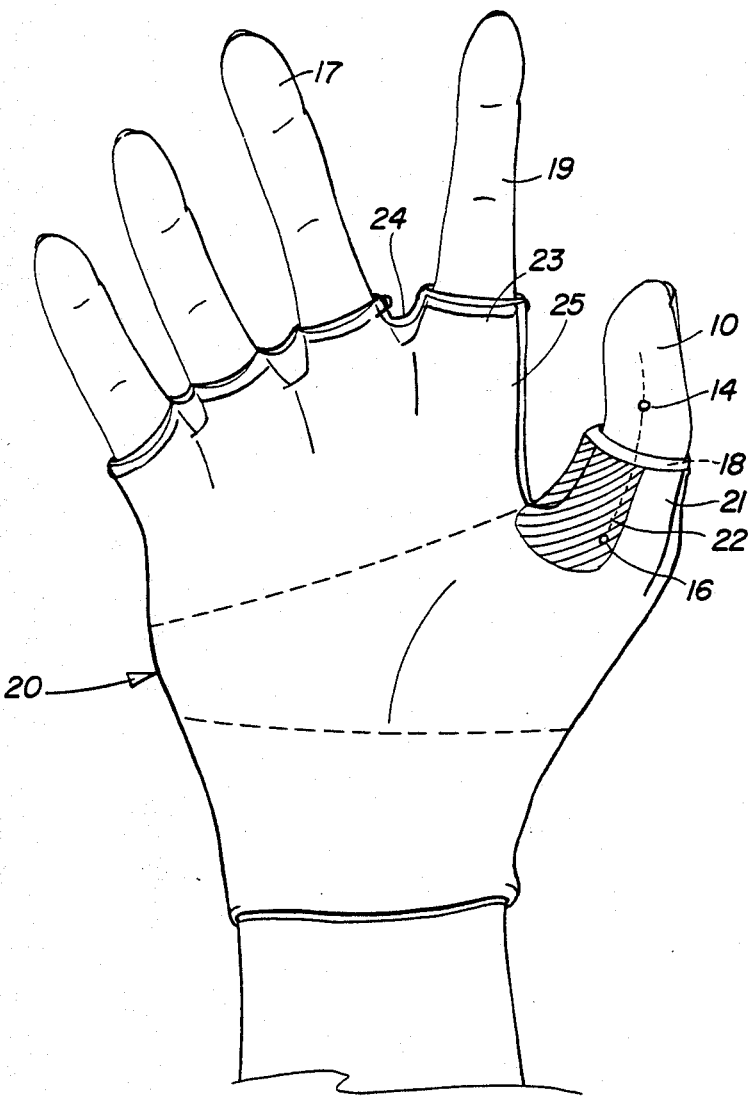
FIG. 2 is a view similar to FIG. 1 showing the dynamic splint of the present invention applied to the hand.

FIG. 2 shows the glove-like dynamic splint of the present invention which is generally designated 20, and which has been found by the inventor to extend or abduct the thumb 10 an even to flex the DIP joint 14. The inventive dynamic splint also causes extension of the index finger 19 from its usually flexed position.

The glove 20 comprises a covering made of stretch material, such as stretch fabric. This material may be synthetic, such as nylon, polyester, or rayon, or may be natural, such as cotton with the inclusion of rubber or other elastic material therein to achieve a stretching function. Surgical grade stretching fabric is also available in different weights to exert different stretching forces. The glove can be made of stretch fabric having a weight tailored to size and strength of the hand. Heavier weight materials can be used, for example for adults, with lighter weights being used for children. For cosmetic reasons, the covering may have a flesh color.

The inventor has found during clinical treatments with the glove, particularly on children, that the children do not seek to remove the glove and find it confortable and agreeable to wear. This of course facilitates treatment of their condition.

The padding is made from cotton and is firm in constistancy.

An important feature of the present invention is the use of padding 22 which is placed in the inside of the glove material over the metcarpal-phalengeal or MCP joint 16. Pad 22 also extends over the proximal phalanx region 18 of the thumb, which is almost entirely covered by the pad 22.

The covering of glove 20 also includes at least one sleeve 21 having a hole therethrough, through which thumb 10 extends. The embodiment of FIG. 2 includes an additional sleeve 23 for index finger 19 and additional sleeves for the remaining fingers including finger 17 which is immediately adjacent to the index finger 19.

The inventor has found that by providing an accumulation of material or an additional padding at 23 around the base of each finger, the index finger tends to extend from its flexed and otherwise useless position. The accumulation or bulk of material, or an additional padding at 23 is positioned around the base of the fingers.

Accumulation of material may also be provided around the base of the remaining fingers. This has been found by the inventor to abduct or spread apart all the fingers and to help extend the index finger and thus bring the hand to an even better position for grasping. The abducting property also causes a general relaxation of spasticity in the hand, as documented by neurological principles.

While the glove in FIG. 2 is shown with collars of material around each of the fingers, the invention includes a configuration, shown in dotted line, where only one sleeve 21 is provided around he thumb 10.

Figure 3:
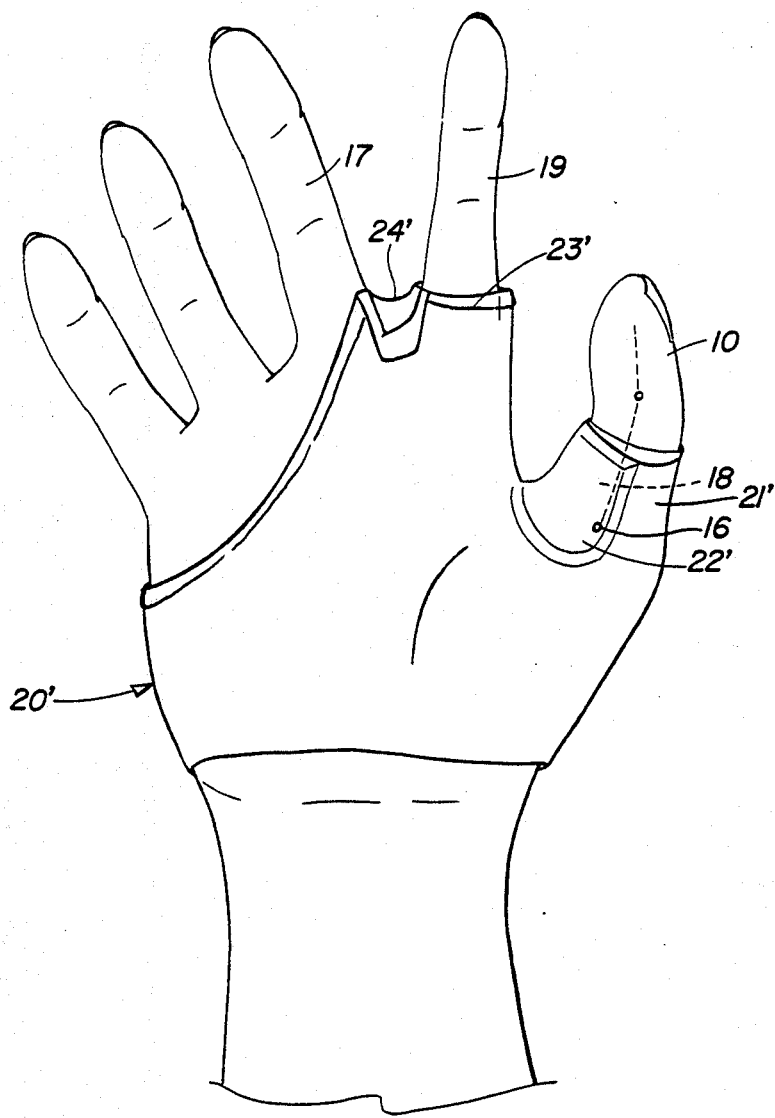
FIG. 3 is a view similar to FIG. 2 showing another embodiment of the dynamic splint applied to the hand.

FIG. 3 shows an alternate embodiment of the invention where the glove 20' includes two sleeves 21' and 23'. A collar of material is provided around finger 19. Sleeve 21' also also carries a padding 22', preferably on the inside surface of the stretch fabric covering material. The covering material includes portions covering parts of the palm and parts of the back of the hand as in the embodiment of FIG. 2. This embodiment is advantageous over the embodiment shown in dotted lines in FIG. 2 in that it treats people with a tendency to flex the index finger.

While specific embodiments of the invention have been shown and described in detail to illustrate the application of the principles of the invention, it will be understood that the invention may be embodied otherwise without departing from such principles.

What is claimed is:

1. A dynamic splint for treating the hands of a person having a spastic condition causing thumb adduction and hyperextension comprising a covering made entirely of elastic stretch fabric material adapted for covering the palm and the back of the person's hand, said covering having at least one sleeve portion with an opening therethrough adapted for the thumb, said sleeve portion adapted for at least partly covering the metacarpal and proximal phalanx of the thumb, said covering including at least one web portion adapted for extending between the thumb and the index finger of the person's hand, and a pad connected to said covering and in a position adapted for engaging over the metacarpal-phalangeal joint of the thumb of the person's hand whereby the thumb is held in an abducted position, said covering including additional sleeve portions adapted for each finger of the person's hand and a collar of material adapted for engagement around the base of each finger of the person's hand, each collar having an accumulation of material.

2. A dynamic splint according to claim 1, wherein said pad is connected on an inside of said covering adapted to lie adjacent the person's thumb.

3. A dynamic splint according to claim 2, wherein the stretch material has a weight which is selected depending on the size and strength of the person's hand.

4. A method of treating a child with a spastic condition causing thumb adduction and hyperextension, comprising applying to the child's hand a dynamic splint comprising a covering made entirely of elastic stretch fabric material adapted for covering the palm and the back of the person's hand, said covering having at least one sleeve portion with an opening therethrough adapted for the thumb, said sleeve portion adapted for at least partly covering the metacarpal and proximal phalanx of the thumb, said covering including at least one web portion adapted for extending between the thumb and the index finger of the person's hand, and a pad connected to said covering and in a position adapted for engaging over the metacarpal-phalangeal joint of the thumb of the person's hand whereby the thumb is held in an abducted position said covering including additional sleeve portions adapted for each finger of the person's hand and a collar of material adapted for engagement around the base of each finger of the person's hand, each collar having an accumulation of material.

* * * * *